United States Patent
Mizushima et al.

(10) Patent No.: US 11,090,282 B2
(45) Date of Patent: Aug. 17, 2021

(54) METHOD FOR MANUFACTURING LONG CHAIN POLYUNSATURATED FATTY ACID-CONTAINING FAT

(71) Applicant: FUJI OIL HOLDINGS INC., Osaka (JP)

(72) Inventors: Shigeki Mizushima, Tsukubamirai (JP); Masaharu Kato, Tsukubamirai (JP); Makiko Kojima, Tsukubamirai (JP)

(73) Assignee: FUJI OIL HOLDINGS INC., Osaka (JP)

( * ) Notice: Subject to any disclaimer, the term of this patent is extended or adjusted under 35 U.S.C. 154(b) by 498 days.

(21) Appl. No.: 15/567,475

(22) PCT Filed: Apr. 25, 2016

(86) PCT No.: PCT/JP2016/062919
§ 371 (c)(1),
(2) Date: Oct. 18, 2017

(87) PCT Pub. No.: WO2016/175169
PCT Pub. Date: Nov. 3, 2016

(65) Prior Publication Data
US 2018/0050007 A1    Feb. 22, 2018

(30) Foreign Application Priority Data

Apr. 27, 2015 (JP) .............................. JP2015-090532

(51) Int. Cl.

| | |
|---|---|
| *A61K 31/202* | (2006.01) |
| *A23D 9/02* | (2006.01) |
| *C11C 3/00* | (2006.01) |
| *C11B 5/00* | (2006.01) |
| *A23D 9/06* | (2006.01) |
| *A23L 33/12* | (2016.01) |
| *A61K 36/53* | (2006.01) |
| *A23L 33/105* | (2016.01) |
| *A23L 17/00* | (2016.01) |
| *A23L 27/10* | (2016.01) |

(52) U.S. Cl.
CPC .............. *A61K 31/202* (2013.01); *A23D 9/02* (2013.01); *A23D 9/06* (2013.01); *A23L 17/00* (2016.08); *A23L 27/10* (2016.08); *A23L 33/105* (2016.08); *A23L 33/12* (2016.08); *A61K 36/53* (2013.01); *C11B 5/0085* (2013.01); *C11C 3/00* (2013.01); *A23V 2002/00* (2013.01); *A61K 2236/15* (2013.01)

(58) Field of Classification Search
CPC ........ A23L 33/12; A23L 33/105; A23L 27/10; A23L 17/00; A61K 31/002; A61K 36/53; A61K 2236/15; A23D 9/06; A23D 9/02; C11C 3/00; C11B 5/0085
See application file for complete search history.

(56) References Cited

U.S. PATENT DOCUMENTS

| | | | |
|---|---|---|---|
| 4,525,306 A | 6/1985 | Yajima | |
| 5,492,709 A | 2/1996 | Aeschbach et al. | |
| 5,585,130 A | 12/1996 | Aeschbach et al. | |
| 6,261,608 B1 | 7/2001 | Lee et al. | |
| 6,623,774 B2 | 9/2003 | Kendrick et al. | |
| 9,637,706 B2 | 5/2017 | Indrasena | |
| 2002/0164413 A1* | 11/2002 | Van Boom | A23D 9/04 426/613 |
| 2003/0161918 A1 | 8/2003 | Kendrick et al. | |
| 2006/0111578 A1* | 5/2006 | Arhancet | A23B 9/22 554/8 |
| 2010/0130610 A1* | 5/2010 | Keller | C11B 3/14 514/560 |
| 2015/0175934 A1 | 6/2015 | Indrasena | |

FOREIGN PATENT DOCUMENTS

| | | |
|---|---|---|
| CN | 103351946 | 10/2013 |
| GB | 2 107 344 | 4/1983 |
| JP | 2-189394 | 7/1990 |
| JP | 9-111237 | 4/1997 |
| JP | 9-235584 | 9/1997 |
| JP | 2000-96077 | 4/2000 |
| JP | 2002-212586 | 7/2002 |

(Continued)

OTHER PUBLICATIONS

Tsimidou et al., "Evaluation of Oregano Antiocidant Activity in Mackerel Oil". Food Research International. vol. 28, No. 4, pp. 431-433. (Year: 1995).*
"Rosemary Production". from https://www.nda.agric.za/docs/Brochures/ProGuiRosemary.pdf (Year: 2012).*
Extended European Search Report dated Oct. 9, 2018 in corresponding European Patent Application No. 1678446.1.
Tsimidou et al., "Evaluation of oregano antioxidant activity in mackerel oil", Food Research International, 28(4):431-433 (1995).

(Continued)

*Primary Examiner* — Erik Kashnikow
*Assistant Examiner* — Assaf Zilbering
(74) *Attorney, Agent, or Firm* — Wenderoth, Lind & Ponack, L.L.P.

(57) ABSTRACT

Oxidation stability is improved and a long chain polyunsaturated fatty acid-containing fat with a good flavor is obtained with a method for manufacturing a long chain polyunsaturated fatty acid-containing fat with a moisture content of 3 weight % or less, the method comprising a step for treatment by contact with rosemary. Consequently, it is possible to limit the generation of reversion flavor, unpleasant odors, and peroxides that have health-harming effects over long periods and to provide a highly healthy long chain polyunsaturated fatty acid-containing fat at less cost than in the past. By adding a relatively small amount of an antioxidant substance, oxidation stability can be further improved.

12 Claims, No Drawings

(56) References Cited

FOREIGN PATENT DOCUMENTS

| | | | |
|---|---|---|---|
| JP | 2003-516466 | 5/2003 | |
| JP | 3927609 | 6/2007 | |
| JP | 2007-185138 | 7/2007 | |
| JP | 4129344 | 8/2008 | |
| JP | 2013-203768 | 10/2013 | |
| JP | 2015-40297 | 3/2015 | |
| TW | 201338707 | 10/2013 | |
| WO | 2014/022505 | 2/2014 | |
| WO | WO-2014022505 A1 * | 2/2014 | ........... C11B 5/0092 |

OTHER PUBLICATIONS

Antoun et al., "Gourmet olive oils: stability and consumer acceptability studies", Food Research International, 30(2):131-136 (1997).
Watanabe et al., "The Antioxidative Activities of Distilled Water-Soluble and Ethanol-Soluble Fractions from Ground Spices", Journal of Japanese Society of Food and Nutrition, 27(4):181-183 (1974), with English Abstract.
"Let's make oil", Nov. 19, 2015 uploaded, [Retrieved on Mar. 14, 2017], Retrieved from the internet: <URL:http://www5e.biglobe.ne.jp/~occultyo/siryou/oil.htm> (with its English partial translation).
"Herb filtration (cold leaching of purple root)", Mar. 12, 2015 uploaded, [Retrieved on Mar. 14, 2017], Retrieved from the internet: URL:http://kobe-egarden.net/%E3%83%8F%E3%83%BC%E3%83%96%E6%88%90%E5%88%86%E3%81%AE%E6%8A%BD%E5%87%BA/post-2748/ (with its English partial translation).
Office Action dated Jan. 10, 2017 in Japanese Application No. 2016-563010, with English Translation.
Office Action dated Mar. 28, 2017 in Japanese Application No. 2016-563010, with English Translation.
International Preliminary Report on Patentability dated Oct. 31, 2017 in International (PCT) Application No. PCT/JP2016/062919.
International Search Report dated Jun. 7, 2016 in International (PCT) Application No. PCT/JP2016/062919.
Oilmaker (Primary Intermediate Advanced), Department of Personnel, State Food Administration, China Light Industry Press, Jan. 2007, pp. 322-323, 409-410, with partial English translation.
First Chinese Office Action dated Feb. 28, 2020 issued in corresponding Chinese Patent Application No. 201680024122.1, with English machine translation, and search report.

* cited by examiner

METHOD FOR MANUFACTURING LONG CHAIN POLYUNSATURATED FATTY ACID-CONTAINING FAT

TECHNICAL FIELD

The present invention relates to a process for producing a long-chain polyunsaturated fatty acid-containing fat. In more detail, the present invention relates to a process for producing a long-chain polyunsaturated fatty acid-containing fat which implements improvement of oxidation stability, which is required from a food containing a long-chain polyunsaturated fatty acid-containing fat.

BACKGROUND ART

In recent years, it has been known that fats containing a long-chain polyunsaturated fatty acid have a physiological action, and these fats are also widely used for usage for addition into health foods and feed from health consciousness. Especially, n-3 long-chain polyunsaturated fatty acids containing 5 to 6 double bonds, such as eicosapentaenoic acid (EPA) and docosahexaenoic acid (DHA), have been reported to have a large number of actions such as decrease in neutral fat and cholesterol in the blood, alleviation of symptoms of rheumatoid arthritis, prevention of formation of a thrombus and anti-allergenic action, and have come to be recognized as a functional food by many consumers. Herein, the fat containing a long-chain polyunsaturated fatty acid is written as a long-chain polyunsaturated fatty acid-containing fat. In 2005, Ministry of Health, Labor and Welfare has determined a recommended practical intake level of EPA and DHA (for adult) as 1 g/day of total amount. Thus, a use of fat containing a large amount of EPA and DHA is desired. Such long-chain polyunsaturated fatty acid-containing fat has very worse oxidation stability as compared with that of edible oils such as soybean oil and rapeseed oil, and is easily oxidized by oxygen, heat, light and the like, to produce a peroxide substance of which adverse effect on the health is concerned. In addition, its practical use is remarkably limited because off-taste and off-flavor like fish is felt from the initial stage of the oxidation.

For this reason, techniques for improving an oxidation stability of fat have been studied. For example, a method of adding roasted sesame oil, ascorbic acid ester, herbal extract to fat containing polyunsaturated fatty acid to stabilize the fat (Patent Document 1), a lipophilic antioxidant containing Chinese bayberry extract and rosemary extract (Patent Document 2), a method of adding tocopherol, ascorbic acid and tea extract (Patent Document 3), and a method of adding ascorbic acid or derivative thereof and another organic acid or derivative thereof (Patent Document 4) are known. However, these techniques are insufficient for improving the oxidation stability of a long-chain polyunsaturated fatty acid-containing fat. Thus, further excellent antioxidant method is desired.

A rosemary itself is known to have high antioxidant properties. For example, a method including contacting fat and plant material rich in phenolic antioxidant at high temperature and mixing under the presence of 10 to 20% by weight of water with respect to the plant material, and then pressing the mixture under a 40 bar or more, is disclosed (Patent Document 5). However, a long-chain polyunsaturated fatty acid-containing fat produced by the above method has extremely strong smell, and therefore the adding amount should be limited. Therefore, a rosemary extract in which antioxidant ingredients are concentrated and having reduced smell is widely used as an antioxidant instead of using the rosemary powder used as a spice. However, the smell peculiar to rosemary is felt when the rosemary extract is used for fat even if the rosemary extract has reduced smell. Thus, there is a problem that the rosemary extract has limited range of purpose. Meanwhile, Patent Document 6 discloses a method of producing a fat having high oxidation stability and excluding the problem of smell peculiar to rosemary extract or sage extract, including subjecting a fish oil treated with silica gel to vacuum steam deodorization in the presence of rosemary extract or sage extract, and adding palmitic acid ascorbic acid ester or mixed tocopherol. In addition, Patent Document 7 discloses a method of producing a fat having high oxidation stability and excluding the problem of smell peculiar to rosemary extract or sage extract, including adding rosemary extract to a long-chain polyunsaturated fatty acid-containing fat, and then subjecting to deodorization treatment in which steam is contacted at less than 140° C.

PRIOR ART DOCUMENTS

Patent Documents

Patent Document 1: JP H02-189394 A
Patent Document 2: JP 2007-185138 A
Patent Document 3: JP H09-111237 A
Patent Document 4: JP H09-235584 A
Patent Document 5: JP 3927609 B
Patent Document 6: JP 4129344 B
Patent Document 7: JP 2015-40297 A

SUMMARY OF INVENTION

Problems to be Solved by Invention

As described above, Patent Document 1 and Patent Document 2 disclose production methods using a rosemary extract effective for improving a flavor of a long-chain polyunsaturated fatty acid. These techniques have seemed to be versatile techniques to enhance an oxidation stability of a long-chain polyunsaturated fatty acid. However, it is found that these methods are insufficient for suppressing an increase in peroxide value (POV), which is important in edible use.

In addition, as a method for increasing the content of long-chain polyunsaturated fatty acids and improving oxidation stability, methods, such as treating an edible marine animal or vegetable oil with silica gel using a rosemary extract (Patent Document 6), and performing a step of deodorization treatment by contacting with steam at less than 140° C. (Patent Document 7), are insufficient as a method for improving an oxidation stability of a long-chain polyunsaturated fatty acid-containing oil. Thus, more excellent method for preventing an oxidation is desired. In addition, these production methods use a rosemary extract. The rosemary extract is relatively expensive as compared with rosemary (powder), which is used as a spice, because the extract needs a step of extraction and a step of removing the extraction solvent and a step of evaporating the extraction solvent. Thus, an establishment of a simple and inexpensive production method is desired.

Means for Solving Problems

The inventors have extensively studied for solving the above problems. As a result, they have found that an oxidation stability of a long-chain polyunsaturated fatty acid-containing fat is surprisingly improved by treating the fat by contacting with a rosemary itself, which is generally used as a spice. The present invention has been completed based on the finding.

That is, the present invention is:

(1) a process for producing a long-chain polyunsaturated fatty acid-containing fat, including a step of contacting a fat with a rosemary, where the fat contains 3% by weight or less of water;

(2) the process for producing a long-chain polyunsaturated fatty acid-containing fat of (1), where the rosemary is a dried product of a leaf of Lamiaceae, genus *Rosmarinus*, or a pulverized product of the dried product;

(3) the process for producing a long-chain polyunsaturated fatty acid-containing fat of (1) or (2), further including a step of filtration after the step of contacting with the rosemary;

(4) the process for producing a long-chain polyunsaturated fatty acid-containing fat of any of (1) to (3), further including a step of bleaching before or at the same time of the step of contacting with the rosemary with stirring, and further including a step of filtration after the step of bleaching and a step of steam deodorization under reducing pressure after the step of filtration;

(5) the process for producing a long-chain polyunsaturated fatty acid-containing fat of any of (1) to (4), where the water content in the fat is maintained at 3% by weight or less from the step of contacting with rosemary to the step of steam deodorization;

(6) the process for producing a long-chain polyunsaturated fatty acid-containing fat of (4) or (5), where a deodorization temperature is 170° C. or more and the deodorization temperature meets the following formula, (deodorization temperature−170° C.)×(deodorization temperature−170° C.)×deodorization time (min)/100=100 or less;

(7) the process for producing a long-chain polyunsaturated fatty acid-containing fat of any of (4) to (6), where the step of bleaching is performed by adding 0.5% by weight or more of rosemary and 1% by weight or more of activated earth;

(8) the process for producing a long-chain polyunsaturated fatty acid-containing fat of any of (1) to (7), further including a step of absorbing with activated carbon;

(9) the process for producing a long-chain polyunsaturated fatty acid-containing fat of (8), where the step of bleaching is performed by adding 0.5% by weight or more of rosemary, 1% by weight or more of activated earth, and 1% by weight or more of activated carbon;

(10) the process for producing a long-chain polyunsaturated fatty acid-containing fat of any of (1) to (9), where the rosemary is a rosemary powder obtained by drying a leaf of Lamiaceae, genus *Rosmarinus* and pulverizing the dried leaf;

(11) the process for producing a long-chain polyunsaturated fatty acid-containing fat of any of (1) to (10), where the fat contains 20% by weight or more of long-chain polyunsaturated fatty acid having 5 or more double bonds in a constituent fatty acid composition;

(12) the process for producing a long-chain polyunsaturated fatty acid-containing fat of any of (8) to (11), where the activated carbon is treated by chemical activation;

(13) the process for producing a long-chain polyunsaturated fatty acid-containing fat of (12), where the chemical activation is phosphoric acid activation;

(14) the process for producing a long-chain polyunsaturated fatty acid-containing fat of any of (4) to (13), where peroxide value of the long-chain polyunsaturated fatty acid-containing fat after the step of steam deodorization is 14 meq/kg or less measured by the following storage test for a long-chain polyunsaturated fatty acid-containing fat:

(Storage Test for a Long-Chain Polyunsaturated Fatty Acid-Containing Fat)

pouring 50 g of uniformly mixed fat into 100 ml glass container and then sealing the container,
    storing the glass container at 40° C. for 14 days, and
    measuring peroxide value of the fat after 14 days storage.

Effects of Invention

The present invention enables to obtain a long-chain polyunsaturated fatty acid-containing fat having improved oxidative stability and good flavor by a simple method. Especially, the long-chain polyunsaturated fatty acid-containing fat obtained by the production process of the present invention provides good values in flavor evaluation and peroxide value, which is an index of oxidative stability of fat, after storage, by subjecting the fat to steam deodorization with appropriate thermal history, as well as the fat immediately after the production has good flavor. Thus, a long-chain polyunsaturated fatty acid-containing fat having high health advantages can be inexpensively used by suppressing a generation of peroxide, which generates reversion odor and unpleasant odor and is bad for health, over a long period of time. Further, by adding relatively small amount of antioxidant, it is possible to further improve the oxidative stability.

Moreover, the long-chain polyunsaturated fatty acid-containing fat obtained by the production process of the present invention may be distributed in liquid form because it is not necessary to be encapsulated, emulsified or powdered for the purpose of avoiding contact with air, in contrast with the conventional long-chain polyunsaturated fatty acid-containing fat. Of course, the fat may be used without limiting to the application range in the liquid form. More specifically, the long-chain polyunsaturated fatty acid-containing fat obtained by the production process of the present invention may be formed to an emulsion, or processed to powder form or capsule form. Thus, the fat may be used for broader applications, including the use range of conventional long-chain polyunsaturated fatty acid-containing fat.

Mode for Carrying Out Invention

A raw material of rosemary that may be used in the present invention is an evergreen shrub of the Lamiaceae rosemary (*Rosmarinus officinalis* Linne). Rosemary is originally used as a spice, and it is used as a spice for meat dishes by taking advantage of the strong aroma from the rosemary. Generally, rosemary extract, which is extracted from rosemary, is used as an antioxidant. It is known that water-soluble or water-insoluble rosemary extract may be obtained due to an extraction solvent or a method of treating the extract liquid.

In the present invention, rosemary not subjected to the extraction treatment is used. In addition, a site of rosemary to be used is not particularly limited, such as whole plant, leaf, root, stem, flower, fruit, seed, and mixture thereof. Preferably, leaf is used. In this case, dried leaf is preferable. Both dried leaf and dried leaf powder may be used. Dried leaf without subjecting to pulverization may be used because the dried leaf is sheared and mixed into fat in the production process of the present invention. From the point of good contact efficiency to fat, rosemary powder, for example, obtainable by pulverizing dried leaf, is preferable.

The present invention includes the above-mentioned step of contact treatment with rosemary. The step of contact treatment with rosemary is not particularly limited as long as rosemary is contacted, such as stirring contact treatment and column contact treatment. Preferably a stirring contact treatment is used, and a step of filtration is carried out after the stirring contact treatment with rosemary. The step of filtration is not particularly limited as long as rosemary is filtered off. For example, filtration apparatus used in a step of bleaching fat may be used. Examples of the filtration apparatus used in the step of bleaching fat include filter press and leaf filter. Filtration may be carried out at 1.0 MPa or less, generally about 0.5 MPa of filtration pressure. When filtration is carried out in a small scale such as laboratory, filtration may be carried out similarly to the filtration method for a fat after bleaching, such as suction filtration with a filter paper.

Water content in the long-chain polyunsaturated fatty acid-containing fat of the present invention is 3% by weight or less, preferably 2% by weight or less, more preferably 1% by weight or less. When the water content is more than 3% by weight, yield loss may occur due to hydrolysis during production etc., and thus, it is not preferable. More preferably, it is preferable to maintain the water content in the fat from the step of contact treatment with rosemary to the end of the step of steam deodorization.

The long-chain polyunsaturated fatty acid-containing fat used in the present invention contains a long-chain polyunsaturated fatty acid having 5 or more double bonds and 20 or more carbon atoms. A kind of fatty-acid having 5 or more double bonds is not particularly limited. Examples of such fatty acid include docosahexaenoic acid (DHA; C22:6), eicosapentaenoic acid (EPA; C20:5), and docosapentaenoic acid (DPA; C22:5). A content of long-chain polyunsaturated fatty acid in the constituent fatty acid composition is preferably 20% by mass or more. Examples of such fat include various animal and vegetable oil such as fish oil and vegetable oil, oil obtained from microorganism or algae. When the content of long-chain polyunsaturated fatty acid is less than 20% by mass, it is not preferable in terms of cost and production efficiency. The present invention may also be effective for a long-chain polyunsaturated fatty acid-containing fat formulation obtained by mixing two or more kinds of fat including the long-chain polyunsaturated fatty acid-containing fat of the present invention and other fat.

In the present invention, an adding amount of rosemary is preferably 0.5% by weight or more, more preferably 1% by weight or more with respect to the fat. When the adding amount of rosemary is less than 0.5% by weight, insufficient stability is provided. The higher adding amount provides more effect. However, when the adding amount is too large, the efficiency becomes lower as compared with the effect obtained. Thus, the adding amount is preferably 10% by weight or less, more preferably 5% by weight or less. It may not fully effective when the adding amount is more than 10% by weight.

In a preferred embodiment of the present invention, the step of contact treatment with rosemary is a stirring contact treatment before or simultaneously with bleaching treatment. In addition, the embodiment includes the step of filtration after the step of bleaching, and the step of steam deodorization under reducing pressure after the step of filtration. From the point of efficiently producing, it is more preferable to carry out the step of contact treatment with rosemary simultaneously with the step of bleaching.

In the present invention, an adding amount of activated earth in the step of bleaching is preferably 1% by weight or more, more preferably 3% by weight or more. When the amount of activated earth is less than 1% by weight, it is not preferable because fish odor and so-called reversion odor, in which rosemary specific metal odor is generated, is generated after storage of the fat. The higher adding amount provides more effect. However, when the adding amount is too large, the efficiency becomes lower as compared with the effect obtained. Thus, the adding amount is preferably 5% by weight or less. When the adding amount is more than 5% by weight, the quality of the obtained product is not significantly improved and the yield might be lowered by wasting the fat remaining in the activated earth with removing the activated earth in the step of filtration, and thus it is not preferable. The adding amount of activated earth is suitably adjusted as determined by color tone of raw material fat.

In the step of steam deodorization in the present invention, it is more preferable that the thermal history conditions of the step of steam deodorization meet the following formula. The thermal history is determined by the following formula from deodorization temperature and deodorization time. The deodorization temperature is preferably 170° C. or more, more preferably 180° C. When the deodorization temperature is less than 170° C., it is not preferable because fish odor and oil odor might remain in the fat. In addition, the vacuum degree is preferably 0.8 kPa or less, more preferably 0.6 kPa or less, further preferably 0.4 kPa or less.

Thermal history=(deodorization temperature−170° C.)×(deodorization temperature−170° C.)×deodorization time (minutes)/1000

In the present invention, a condition of thermal history is preferable to thermal history=100 or less, more preferably 50 or less. When the thermal history condition is more than 100, it is not preferable because the long-chain polyunsaturated fatty acid content might be lowered in the step of deodorization. The adding amount of steam in the step of steam deodorization is preferably 1% by weight or more, more preferably 3% by weight or more with respect to fat. When the adding amount of steam is less than 1% by weight, fish odor or oil odor may remain in the fat, and it is not preferable.

A preferred embodiment of the present invention includes a step of adsorption treatment with activated carbon. The amount of activated carbon to fat is preferably 0.5% by weight or more, more preferably 1% by weight or more. The amount is preferably 4% by weight or less because it is inefficient in comparison with the obtained effect. When 4% by weight or more of activated carbon is added, an effect of suppressing reversion order may not be improved, and thus, it is not preferable from the viewpoint of cost-effectiveness. A conventional activated carbon may be used. Preferably, the activated carbon is treated by chemical activation, more preferably, phosphoric acid activation. The activated carbon treated with chemical activation may be prepared by subjecting a raw material, such as sawdust, wood chip, bamboo, coconut shell, and coal, to activation treatment with chemical, such as phosphoric acid, zinc chloride, sulfuric acid, calcium chloride, sodium hydroxide, and potassium hydroxide. Among them, the activated carbon treated with phosphoric acid enables to efficiently suppress a reversion odor with a small amount of the adsorption agent. In terms of the production efficiently, it is more preferable to carry out the step of adsorption treatment with activated carbon simultaneously with the step of bleaching treatment.

In a preferred embodiment of the present invention, peroxide value of the long-chain polyunsaturated fatty acid-containing fat after the step of steam deodorization is preferably 14 meq/kg or less, more preferably 13 meq/kg or less, further preferably 12 meq/kg or less, most preferably 10 meq/kg or less, measured by the following storage test for a long-chain polyunsaturated fatty acid-containing fat:
(Storage Test for a Long-Chain Polyunsaturated Fatty Acid-Containing Fat)
 pouring 50 g of uniformly mixed fat into 100 ml glass container and then sealing the container,
 storing the glass container at 40° C. for 14 days, and
 measuring peroxide value of the fat after 14 days storage.

An oxidation inhibitor may be added to the long-chain polyunsaturated fatty acid-containing fat of the present invention. Examples of the oxidation inhibitor include tocopherol, water-soluble antioxidative substance such as *myrica* extract, rosemary extract, polyphenol derived from grape juice or tea, ascorbic acid and derivative thereof, gallic acid and derivative thereof. Such oxidation inhibitors may be used in combination. A preferable oxidation inhibitor is at least one kind selected from ascorbic acid, ascorbic acid derivative, tea extract, gallic acid, gallic acid derivative and lecithin.

In addition, an additive, which may be used for an edible fat, such as flavor, coloring agent and silicone may be used for the long-chain polyunsaturated fatty acid-containing fat of the present invention, as necessary.

EXAMPLES

Examples of the present invention will be explained in more detail herein below. In the examples, both of % and part mean weight basis.

In the examples, rosemary powder obtained by grinding the dried leaves of an evergreen shrub of the Lamiaceae rosemary (*Rosmarinus officinalis* Linne) was used as rosemary.
(Sensory Evaluation Method of Long-Chain Polyunsaturated Fatty Acid-Containing Fat)

Long-chain polyunsaturated fatty acid-containing fat immediately after preparation was evaluated with 10-stages sensory evaluation by 10 panelists in the evaluation items for the flavor including oil odor, fish odor and rosemary odor.

A fat showing evaluations as 4 or more in all items was determined as good.

Oil odor: larger number indicates weaker degradation odor of oil, and smaller number indicates stronger degradation odor of oil.

Fish odor: larger number indicates weaker fish odor, and smaller number indicates stronger fish odor.

Rosemary odor: larger number indicates weaker rosemary odor, and smaller number indicates stronger rosemary odor.
(Storage Test for a Long-Chain Polyunsaturated Fatty Acid-Containing Fat)

The test is carried out by:
 pouring 50 g of uniformly mixed fat into 100 ml glass container and then sealing the container,
 storing the glass container at 40° C. for 14 days, and
 measuring peroxide value of the fat after 14 days storage.
(Sensory Evaluation Method of Long-Chain Polyunsaturated Fatty Acid-Containing Fat after Storage)

Long-chain polyunsaturated fatty acid-containing fat degraded by the storage test was evaluated with 10-stages sensory evaluation by 10 panelists in the evaluation items for the flavor including oil odor, fish odor and reversion odor of rosemary (metal flavor).

A fat showing evaluations as 4 or more in all items was determined as good.

Oil odor: larger number indicates weaker degradation odor of oil, and smaller number indicates stronger degradation odor of oil.

Fish odor: larger number indicates weaker fish odor, and smaller number indicates stronger fish odor.

Reversion odor of rosemary: larger number indicates weaker metal flavor, and smaller number indicates stronger metal flavor.

Example 1

To 100 parts of neutralized tuna oil (acid value=0.10, peroxide value=5.5, iodine value=184, EPA+DHA content=28.0%), 1 part of rosemary powder (trade name: Rosemary (powder), manufactured by S & B foods Inc.), and 3.0 parts of activated earth were added. The mixture was subjected to a stirring contact treatment in a step of bleaching under vacuum of 1.6 kPa (12 torr) at 120° C. for 15 minutes. Then, the mixture was filtered with a filter paper (trade name: qualitative filter paper No. 2, manufactured by Toyo Roshi Kaisha, Ltd.). Then, 100 parts of the bleached fat was subjected to steam deodorization treatment under vacuum of 0.4 kPa (3 torr) or less at 160° C. for 180 minutes with adding 3 parts of steam to obtain a long-chain polyunsaturated fatty acid-containing fat.

Substances dissolved into the fat from rosemary powder were 0.2 part. POV of the fat immediately after preparation was 0.2.

During the neutralized tuna oil, the step of rosemary treatment and bleaching, and the step of deodorization, water content in the fat was 0.01 to 0.10%.

The content of EPA and DHA in the long-chain polyunsaturated fatty acid-containing fat, evaluation of flavor immediately after preparation, and storage test were performed. The results are summarized in Table 1.

Example 2

To 100 parts of neutralized tuna oil, 1 part of rosemary powder, and 3.0 parts of activated earth were added. The mixture was subjected to a stirring contact treatment in a step of bleaching under vacuum of 1.6 kPa (12 torr) at 120° C. for 15 minutes. Then, the mixture was filtered with a filter paper. Then, 100 parts of the bleached fat was subjected to steam deodorization treatment under vacuum of 0.4 kPa (3 torr) or less at 220° C. for 90 minutes with adding 3 parts of steam to obtain a long-chain polyunsaturated fatty acid-containing fat.

Substances dissolved into the fat from rosemary powder were 0.2 part.

During the neutralized tuna oil, the step of rosemary treatment and bleaching, and the step of deodorization, water content in the fat was 0.01 to 0.10%.

The thermal history determined by the following formula was 225.0:

Thermal history=(deodorization temperature−170° C.)×(deodorization temperature−170° C.)×deodorization time (minutes)/1000.

POV of the fat immediately after preparation was 0.

The content of EPA and DHA in the long-chain polyunsaturated fatty acid-containing fat, evaluation of flavor immediately after preparation, and storage test were performed in a similar manner as Example 1. The results are summarized in Table 1.

Comparative Example 1

To 100 parts of neutralized tuna oil, 3.0 parts of activated earth was added. The mixture was subjected to a bleaching treatment under vacuum of 1.6 kPa (12 torr) at 120° C. for 15 minutes. Then, the mixture was filtered with a filter paper. Then, 100 parts of the bleached fat was subjected to steam deodorization treatment under vacuum of 0.4 kPa (3 torr) or less at 180° C. for 180 minutes with adding 3 parts of steam to obtain a long-chain polyunsaturated fatty acid-containing fat.

During the neutralized tuna oil, the step of bleaching, and the step of deodorization, water content in the fat was 0.01 to 0.10%.

The thermal history determined by the following formula was 18.0:

Thermal history=(deodorization temperature−170° C.)×(deodorization temperature−170° C.)×deodorization time (minutes)/1000.

POV of the fat immediately after preparation was 0.

The content of EPA and DHA in the long-chain polyunsaturated fatty acid-containing fat, evaluation of flavor immediately after preparation, and storage test were performed in a similar manner as Example 1. The results are summarized in Table 1.

Comparative Example 2

To 100 parts of neutralized tuna oil, 0.2 part of rosemary extract (trade name: RM-21B base, manufactured by Mitsubishi-Chemical Foods Corporation), and 3.0 parts of activated earth were added. The mixture was subjected to a stirring contact treatment in a step of bleaching under vacuum of 1.6 kPa (12 torr) at 120° C. for 15 minutes. Then, the mixture was filtered with a filter paper. Then, 100 parts of the bleached fat was subjected to steam deodorization treatment under vacuum of 0.4 kPa (3 torr) or less at 180° C. for 180 minutes with adding 3 parts of steam to obtain a long-chain polyunsaturated fatty acid-containing fat.

During the neutralized tuna oil, the step of rosemary treatment and bleaching, and the step of deodorization, water content in the fat was 0.01 to 0.10%.

The thermal history determined by the following formula was 18.0:

Thermal history=(deodorization temperature−170° C.)×(deodorization temperature−170° C.)×deodorization time (minutes)/1000.

POV of the fat immediately after preparation was 0.

The content of EPA and DHA in the long-chain polyunsaturated fatty acid-containing fat, evaluation of flavor immediately after preparation, and storage test were performed in a similar manner as Example 1. The results are summarized in Table 1.

Comparative Example 3

To 100 parts of neutralized tuna oil, 0.6 part of rosemary extract (trade name: RM-21B base, manufactured by Mitsubishi-Chemical Foods Corporation), and 3.0 parts of activated earth were added. The mixture was subjected to a stirring contact treatment in a step of bleaching under vacuum of 1.6 kPa (12 torr) at 120° C. for 15 minutes. Then, the mixture was filtered with a filter paper. Then, 100 parts of the bleached fat was subjected to steam deodorization treatment under vacuum of 0.4 kPa (3 torr) or less at 180° C. for 180 minutes with adding 3 parts of steam to obtain a long-chain polyunsaturated fatty acid-containing fat.

During the neutralized tuna oil, the step of rosemary treatment and bleaching, and the step of deodorization, water content in the fat was 0.01 to 0.10%.

The thermal history determined by the following formula was 18.0:

Thermal history=(deodorization temperature−170° C.)×(deodorization temperature−170° C.)×deodorization time (minutes)/1000.

POV of the fat immediately after preparation was 0.

The content of EPA and DHA in the long-chain polyunsaturated fatty acid-containing fat, evaluation of flavor immediately after preparation, and storage test were performed in a similar manner as Example 1. The results are summarized in Table 1.

Comparative Example 4

To 100 parts of neutralized tuna oil, 0.6 part of rosemary extract (trade name: RM-21B base, manufactured by Mitsubishi-Chemical Foods Corporation), and 3.0 parts of activated earth were added. The mixture was subjected to a stirring contact treatment in a step of bleaching under vacuum of 1.6 kPa (12 torr) at 120° C. for 15 minutes. Then, the mixture was filtered with a filter paper. Then, 100 parts of the bleached fat was subjected to steam deodorization treatment under vacuum of 0.4 kPa (3 torr) or less at 130° C. for 60 minutes with adding 3 parts of steam to obtain a long-chain polyunsaturated fatty acid-containing fat. POV of the fat immediately after preparation was 0.7.

During the neutralized tuna oil, the step of rosemary treatment and bleaching, and the step of deodorization, water content in the fat was 0.01 to 0.10%.

The content of EPA and DHA in the long-chain polyunsaturated fatty acid-containing fat, evaluation of flavor immediately after preparation, and storage test were performed in a similar manner as Example 1. The results are summarized in Table 1.

Comparative Example 5

To 100 parts of neutralized tuna oil, 3.0 parts of activated earth was added. The mixture was subjected to a bleaching treatment under vacuum of 1.6 kPa (12 torr) at 120° C. for 15 minutes. Then, the mixture was filtered with a filter paper. Then, 100 parts of the bleached fat was subjected to steam deodorization treatment under vacuum of 0.4 kPa (3 torr) or less at 180° C. for 180 minutes with adding 3 parts of steam to obtain a purified fat. To 100 parts of the purified fat, 0.2 part of rosemary extract was added to obtain a long-chain polyunsaturated fatty acid-containing fat.

During the neutralized tuna oil, the step of bleaching, and the step of deodorization, water content in the fat was 0.01 to 0.10%.

The thermal history determined by the following formula was 18.0:

Thermal history=(deodorization temperature−170° C.)×(deodorization temperature−170° C.)×deodorization time (minutes)/1000.

POV of the fat immediately after preparation was 0.

The content of EPA and DHA in the long-chain polyunsaturated fatty acid-containing fat, evaluation of flavor immediately after preparation, and storage test were performed in a similar manner as Example 1. The results are summarized in Table 1.

Comparative Example 6

To 100 parts of neutralized tuna oil, 3.0 parts of activated earth was added. The mixture was subjected to a bleaching treatment under vacuum of 1.6 kPa (12 torr) at 120° C. for 15 minutes. Then, the mixture was filtered with a filter paper. Then, 100 parts of the bleached fat was subjected to steam deodorization treatment under vacuum of 0.4 kPa (3 torr) or less at 180° C. for 180 minutes with adding 3 parts of steam to obtain a purified fat. To 100 parts of the purified fat, 0.6 part of rosemary extract was added to obtain a long-chain polyunsaturated fatty acid-containing fat.

During the neutralized tuna oil, the step of bleaching, and the step of deodorization, water content in the fat was 0.01 to 0.10%.

The thermal history determined by the following formula was 18.0:

Thermal history=(deodorization temperature−170° C.)×(deodorization temperature−170° C.)×deodorization time (minutes)/1000.

POV of the fat immediately after preparation was 0.

The content of EPA and DHA in the long-chain polyunsaturated fatty acid-containing fat, evaluation of flavor immediately after preparation, and storage test were performed in a similar manner as Example 1 The results are summarized in Table 1.

Comparative Examples 2 and 3 showed remarkable deteriorated quality after storage.

Comparative Example 4 showed remarkable poor flavor immediately after preparation.

Comparative Examples 5 and 6 showed remarkable poor flavor due to rosemary odor immediately after preparation.

Example 3

To 100 parts of neutralized tuna oil, 1 part of rosemary powder, and 3 parts of activated earth were added. The mixture was subjected to a stirring contact treatment in a step of bleaching under vacuum of 1.6 kPa (12 torr) at 120° C. for 15 minutes. Then, the mixture was filtered with a filter paper. Then, 100 parts of the bleached fat was subjected to steam deodorization treatment under vacuum of 0.4 kPa (3 torr) or less at 180° C. for 180 minutes with adding 3 parts of steam to obtain a long-chain polyunsaturated fatty acid-containing fat.

Substances dissolved into the fat from rosemary powder were 0.2 part.

During the neutralized tuna oil, the step of rosemary treatment and bleaching, and the step of deodorization, water content in the fat was 0.01 to 0.10%.

The thermal history determined by the following formula was 18.0:

Thermal history=(deodorization temperature−170° C.)×(deodorization temperature−170° C.)×deodorization time (minutes)/1000.

TABLE 1

| | | Example 1 | Example 2 | Comparative Example 1 | Comparative Example 2 | Comparative Example 3 | Comparative Example 4 | Comparative Example 5 | Comparative Example 6 |
|---|---|---|---|---|---|---|---|---|---|
| Step of rosemary treatment and bleaching | Rosemary powder (%) | 1.0 | 1.0 | | | | | | |
| | Rosemary powder (in terms of extract) (%) | 0.2 | 0.2 | | | | | | |
| | Rosemary extract (%) | | | | 0.2 | 0.6 | 0.6 | | |
| | Activated earth (%) | 3.0 | 3.0 | 3.0 | 3.0 | 3.0 | 3.0 | 3.0 | 3.0 |
| Step of deodorization | Temperature (° C.) | 160.0 | 220.0 | 180.0 | 180.0 | 180.0 | 130.0 | 180.0 | 180.0 |
| | Time (min) | 180.0 | 90.0 | 180.0 | 180.0 | 180.0 | 60.0 | 180.0 | 180.0 |
| | Thermal history | — | 225.0 | 18.0 | 18.0 | 18.0 | — | 18.0 | 18.0 |
| Step of adding after blending | Rosemary extract (%) | | | | | | | 0.2 | 0.6 |
| Quality evaluation | EPA + DHA content (%) | 27.9 | 24.0 | 27.5 | 27.4 | 27.5 | 28.0 | 27.4 | 27.4 |
| | EPA + DHA residual ratio in neutralized oil (%) | 99.6 | 85.7 | 98.2 | 97.9 | 98.2 | 100.0 | 97.9 | 97.9 |
| | Oil odor immediately after preparation | 6 | 10 | 10 | 9 | 9 | 1 | 9 | 9 |
| | Fish odor immediately after preparation | 6 | 10 | 10 | 9 | 9 | 1 | 9 | 9 |
| | Rosemary odor immediately after preparation | 6 | 10 | 10 | 9 | 8 | 5 | 3 | 1 |
| | Degradation odor of oil after storage | 5 | 4 | 1 | 2 | 2 | 4 | 4 | 4 |
| | Fish odor after storage | 6 | 4 | 1 | 2 | 2 | 4 | 4 | 4 |
| | Reversion odor of rosemary after storage | 8 | 10 | 10 | 4 | 3 | 3 | 3 | 1 |
| | POV after storage (meq/kg) | 13.4 | 16.6 | 20.0 | 18.2 | 17.6 | 14.9 | 15.7 | 15.0 |

Favorable results were obtained in Examples using rosemary powder both immediately after preparation and after storage.

Comparative Examples 2 to 4 using rosemary extract showed inferior results of flavor evaluation compared to Examples.

POV of the fat immediately after preparation was 0.

The content of EPA and DHA in the long-chain polyunsaturated fatty acid-containing fat, evaluation of flavor immediately after preparation, and storage test were performed in a similar manner as Example 1. The results are summarized in Table 2.

Example 4

To 100 parts of neutralized tuna oil, 3 parts of rosemary powder, and 3 parts of activated earth were added. The mixture was subjected to a stirring contact treatment in a step of bleaching under vacuum of 1.6 kPa (12 torr) at 120° C. for 15 minutes. Then, the mixture was filtered with a filter paper. Then, 100 parts of the bleached fat was subjected to steam deodorization treatment under vacuum of 0.4 kPa (3 torr) or less at 180° C. for 180 minutes with adding 3 parts of steam to obtain a long-chain polyunsaturated fatty acid-containing fat.

Substances dissolved into the fat from rosemary powder were 0.6 part.

During the neutralized tuna oil, the step of rosemary treatment and bleaching, and the step of deodorization, water content in the fat was 0.01 to 0.10%.

The thermal history determined by the following formula was 18.0:

Thermal history=(deodorization temperature−170° C.)×(deodorization temperature−170° C.)×deodorization time (minutes)/1000.

POV of the fat immediately after preparation was 0.

The content of EPA and DHA in the long-chain polyunsaturated fatty acid-containing fat, evaluation of flavor immediately after preparation, and storage test were performed in a similar manner as Example 1. The results are summarized in Table 2.

Example 5

To 100 parts of neutralized tuna oil, 5 parts of rosemary powder, and 3 parts of activated earth were added. The mixture was subjected to a stirring contact treatment in a step of bleaching under vacuum of 1.6 kPa (12 torr) at 120° C. for 15 minutes. Then, the mixture was filtered with a filter paper. Then, 100 parts of the bleached fat was subjected to steam deodorization treatment under vacuum of 0.4 kPa (3 torr) or less at 180° C. for 180 minutes with adding 3 parts of steam to obtain a long-chain polyunsaturated fatty acid-containing fat.

Substances dissolved into the fat from rosemary powder were 1.0 part.

During the neutralized tuna oil, the step of rosemary treatment and bleaching, and the step of deodorization, water content in the fat was 0.01 to 0.10%.

The thermal history determined by the following formula was 18.0:

Thermal history=(deodorization temperature−170° C.)×(deodorization temperature−170° C.)×deodorization time (minutes)/1000.

POV of the fat immediately after preparation was 0.

The content of EPA and DHA in the long-chain polyunsaturated fatty acid-containing fat, evaluation of flavor immediately after preparation, and storage test were performed in a similar manner as Example 1. The results are summarized in Table 2.

Example 6

To 100 parts of neutralized tuna oil, 1 part of rosemary powder, and 3 parts of activated earth were added. The mixture was subjected to a stirring contact treatment in a step of bleaching under vacuum of 1.6 kPa (12 torr) at 120° C. for 15 minutes. Then, the mixture was filtered with a filter paper. Then, 100 parts of the bleached fat was subjected to steam deodorization treatment under vacuum of 0.4 kPa (3 torr) or less at 170° C. for 360 minutes with adding 3 parts of steam to obtain a long-chain polyunsaturated fatty acid-containing fat.

Substances dissolved into the fat from rosemary powder were 0.2 part.

During the neutralized tuna oil, the step of rosemary treatment and bleaching, and the step of deodorization, water content in the fat was 0.01 to 0.10%.

The thermal history determined by the following formula was 0:

Thermal history=(deodorization temperature−170° C.)×(deodorization temperature−170° C.)×deodorization time (minutes)/1000.

POV of the fat immediately after preparation was 0.

The content of EPA and DHA in the long-chain polyunsaturated fatty acid-containing fat, evaluation of flavor immediately after preparation, and storage test were performed in a similar manner as Example 1. The results are summarized in Table 2.

Example 7

To 100 parts of neutralized tuna oil, 1 part of rosemary powder, 1.5 parts of activated earth, and 1.5 parts of activated carbon (trade name: Ume-Hachi brand activated carbon SKE, manufactured by Taihei Chemical Industrial Co., Ltd.) were added. The mixture was subjected to a stirring contact treatment in a step of bleaching under vacuum of 1.6 kPa (12 torr) at 120° C. for 15 minutes. Then, the mixture was filtered with a filter paper. Then, 100 parts of the bleached fat was subjected to steam deodorization treatment under vacuum of 0.4 kPa (3 torr) or less at 180° C. for 180 minutes with adding 3 parts of steam to obtain a long-chain polyunsaturated fatty acid-containing fat.

Substances dissolved into the fat from rosemary powder were 0.2 part.

During the neutralized tuna oil, the step of rosemary treatment and bleaching, and the step of deodorization, water content in the fat was 0.01 to 0.10%.

The thermal history determined by the following formula was 18.0:

Thermal history=(deodorization temperature−170° C.)×(deodorization temperature−170° C.)×deodorization time (minutes)/1000.

POV of the fat immediately after preparation was 0.

The content of EPA and DHA in the long-chain polyunsaturated fatty acid-containing fat, evaluation of flavor immediately after preparation, and storage test were performed in a similar manner as Example 1. The results are summarized in Table 2.

Example 8

To 100 parts of neutralized tuna oil, 1 part of rosemary powder, 1.5 parts of activated earth, and 1.5 parts of wood activated carbon with zinc chloride activation (trade name: Ume-Hachi brand activated carbon ZM, manufactured by Taihei Chemical Industrial Co., Ltd.) were added. The mixture was subjected to a stirring contact treatment in a step of bleaching under vacuum of 1.6 kPa (12 torr) at 120° C. for 15 minutes. Then, the mixture was filtered with a filter paper. Then, 100 parts of the bleached fat was subjected to steam deodorization treatment under vacuum of 0.4 kPa (3 torr) or less at 180° C. for 180 minutes with adding 3 parts of steam to obtain a long-chain polyunsaturated fatty acid-containing fat.

Substances dissolved into the fat from rosemary powder were 0.2 part.

During the neutralized tuna oil, the step of rosemary treatment and bleaching, and the step of deodorization, water content in the fat was 0.01 to 0.10%.

The thermal history determined by the following formula was 18.0:

Thermal history=(deodorization temperature−170° C.)×(deodorization temperature−170° C.)×deodorization time (minutes)/1000.

POV of the fat immediately after preparation was 0.

The content of EPA and DHA in the long-chain polyunsaturated fatty acid-containing fat, evaluation of flavor immediately after preparation, and storage test were performed in a similar manner as Example 1. The results are summarized in Table 2.

Example 9

To 100 parts of neutralized tuna oil, 1 part of rosemary powder, 1.5 parts of activated earth, and 1.5 parts of wood activated carbon with phosphoric acid activation (trade name: Ume-Hachi brand activated carbon FN, manufactured by Taihei Chemical Industrial Co., Ltd.) were added. The mixture was subjected to a stirring contact treatment in a step of bleaching under vacuum of 1.6 kPa (12 torr) at 120° C. for 15 minutes. Then, the mixture was filtered with a filter paper. Then, 100 parts of the bleached fat was subjected to steam deodorization treatment under vacuum of 0.4 kPa (3 torr) or less at 180° C. for 180 minutes with adding 3 parts of steam to obtain a long-chain polyunsaturated fatty acid-containing fat.

Substances dissolved into the fat from rosemary powder were 0.2 part.

During the neutralized tuna oil, the step of rosemary treatment and bleaching, and the step of deodorization, water content in the fat was 0.01 to 0.10%.

The thermal history determined by the following formula was 18.0:

Thermal history=(deodorization temperature−170° C.)×(deodorization temperature−170° C.)×deodorization time (minutes)/1000.

POV of the fat immediately after preparation was 0.

The content of EPA and DHA in the long-chain polyunsaturated fatty acid-containing fat, evaluation of flavor immediately after preparation, and storage test were performed in a similar manner as Example 1. The results are summarized in Table 2.

Example 10

To 100 parts of neutralized tuna oil, 3 parts of rosemary powder, 1.5 parts of activated earth, and 1.5 parts of wood activated carbon with phosphoric acid activation were added. The mixture was subjected to a stirring contact treatment in a step of bleaching under vacuum of 1.6 kPa (12 torr) at 120° C. for 15 minutes. Then, the mixture was filtered with a filter paper. Then, 100 parts of the bleached fat was subjected to steam deodorization treatment under vacuum of 0.4 kPa (3 torr) or less at 180° C. for 180 minutes with adding 3 parts of steam to obtain a long-chain polyunsaturated fatty acid-containing fat.

Substances dissolved into the fat from rosemary powder were 0.6 part.

During the neutralized tuna oil, the step of rosemary treatment and bleaching, and the step of deodorization, water content in the fat was 0.01 to 0.10%.

The thermal history determined by the following formula was 18.0:

Thermal history=(deodorization temperature−170° C.)×(deodorization temperature−170° C.)×deodorization time (minutes)/1000.

POV of the fat immediately after preparation was 0.

The content of EPA and DHA in the long-chain polyunsaturated fatty acid-containing fat, evaluation of flavor immediately after preparation, and storage test were performed in a similar manner as Example 1. The results are summarized in Table 2.

Example 11

To 100 parts of neutralized tuna oil, 3 parts of rosemary powder, 1.5 parts of activated earth, and 1.5 parts of wood activated carbon with phosphoric acid activation were added. The mixture was subjected to a stirring contact treatment in a step of bleaching under vacuum of 1.6 kPa (12 torr) at 120° C. for 15 minutes. Then, the mixture was filtered with a filter paper. Then, 100 parts of the bleached fat was subjected to steam deodorization treatment under vacuum of 0.4 kPa (3 torr) or less at 180° C. for 180 minutes with adding 3 parts of steam to obtain a deodorized fat.

Substances dissolved into the fat from rosemary powder were 0.6 part.

During the neutralized tuna oil, the step of rosemary treatment and bleaching, and the step of deodorization, water content in the fat was 0.01 to 0.10%.

Then, 2.0% tea extract-containing aqueous solution was prepared by adding tea extract (trade name: Sunphenon 90S, manufactured by Taiyo Kagaku Co., Ltd.) to water. To 100 parts of the deodorized fat heated to 70° C., 0.02 part of emulsifier (POEM PR-100, manufactured by RIKEN VITAMIN CO., LTD.) was added and dissolved, and then 1.0 part of 2.0% tea extract-containing aqueous solution was added. The mixture was stirred with a Homomixer (TK ROBO MIX, manufactured by Tokushu Kika Kogyo Co., Ltd.) at 10000 rpm for 10 minutes. Then, the mixture was subjected to a dehydration treatment with stirring under vacuum of 10 torr at 50° C. for 30 minutes to obtain a long-chain polyunsaturated fatty acid-containing fat containing 200 ppm of tea extract.

The thermal history determined by the following formula was 18.0:

Thermal history=(deodorization temperature−170° C.)×(deodorization temperature−170° C.)×deodorization time (minutes)/1000.

POV of the fat immediately after preparation was 0.

The content of EPA and DHA in the long-chain polyunsaturated fatty acid-containing fat, evaluation of flavor immediately after preparation, and storage test were performed in a similar manner as Example 1. The results are summarized in Table 2.

Example 12

To 100 parts of neutralized tuna oil, 3 parts of rosemary powder, 1.5 parts of activated earth, and 1.5 parts of wood activated carbon with phosphoric acid activation were added. The mixture was subjected to a stirring contact treatment in a step of bleaching under vacuum of 1.6 kPa (12 torr) at 120° C. for 15 minutes. Then, the mixture was filtered with a filter paper. Then, 100 parts of the bleached fat was subjected to steam deodorization treatment under vacuum of 0.4 kPa (3 torr) or less at 190° C. for 180 minutes with adding 3 parts of steam to obtain a long-chain polyunsaturated fatty acid-containing fat.

Substances dissolved into the fat from rosemary powder were 0.6 part.

During the neutralized tuna oil, the step of rosemary treatment and bleaching, and the step of deodorization, water content in the fat was 0.01 to 0.10%.

The thermal history determined by the following formula was 72.0:

Thermal history=(deodorization temperature−170° C.)×(deodorization temperature−170° C.)×deodorization time (minutes)/1000.

POV of the fat immediately after preparation was 0.

The content of EPA and DHA in the long-chain polyunsaturated fatty acid-containing fat, evaluation of flavor immediately after preparation, and storage test were performed in a similar manner as Example 1. The results are summarized in Table 2.

Example 13

To 100 parts of neutralized tuna oil, 3 parts of rosemary powder, 1.5 parts of activated earth, and 1.5 parts of wood activated carbon with phosphoric acid activation were added. The mixture was subjected to a stirring contact treatment in a step of bleaching under vacuum of 1.6 kPa (12 torr) at 120° C. for 15 minutes. Then, the mixture was filtered with a filter paper. Then, 100 parts of the bleached fat was subjected to steam deodorization treatment under vacuum of 0.4 kPa (3 torr) or less at 215° C. for 30 minutes with adding 3 parts of steam to obtain a long-chain polyunsaturated fatty acid-containing fat.

Substances dissolved into the fat from rosemary powder were 0.6 part.

During the neutralized tuna oil, the step of rosemary treatment and bleaching, and the step of deodorization, water content in the fat was 0.01 to 0.10%.

The thermal history determined by the following formula was 60.8:

Thermal history=(deodorization temperature−170° C.)×(deodorization temperature−170° C.)×deodorization time (minutes)/1000.

POV of the fat immediately after preparation was 0.

The content of EPA and DHA in the long-chain polyunsaturated fatty acid-containing fat, evaluation of flavor immediately after preparation, and storage test were performed in a similar manner as Example 1. The results are summarized in Table 2.

TABLE 2

| | | Example | | | | | | | | | | |
|---|---|---|---|---|---|---|---|---|---|---|---|---|
| | | 3 | 4 | 5 | 6 | 7 | 8 | 9 | 10 | 11 | 12 | 13 |
| Step of rosemary treatment and bleaching | Rosemary powder (%) | 1.0 | 3.0 | 5.0 | 1.0 | 1.0 | 1.0 | 1.0 | 3.0 | 3.0 | 3.0 | 3.0 |
| | Rosemary powder (in terms of extract) (%) | 0.2 | 0.6 | 1.0 | 0.2 | 0.2 | 0.2 | 0.2 | 0.6 | 0.6 | 0.6 | 0.6 |
| | Activated earth (%) | 3.0 | 3.0 | 3.0 | 3.0 | | 1.5 | 1.5 | 1.5 | 1.5 | 1.5 | 1.5 |
| | Activated carbon (%) | | | | | 1.5 | | | | | | |
| | Wood activated carbon with zinc chloride activation (%) | | | | | | 1.5 | | | | | |
| | Wood activated carbon with phosphoric acid activation (%) | | | | | | | 1.5 | 1.5 | 1.5 | 1.5 | 1.5 |
| Step of deodorization | Temperature (° C.) | 180 | 180 | 180 | 170 | 180 | 180 | 180 | 180 | 180 | 190 | 215 |
| | Time (min) | 180 | 180 | 180 | 360 | 180 | 180 | 180 | 180 | 180 | 180 | 30 |
| | Thermal history | 18.0 | 18.0 | 18.0 | 0.0 | 18.0 | 18.0 | 18.0 | 18.0 | 18.0 | 72.0 | 60.8 |
| | Tea extract (%) | | | | | | | | | 0.02 | | |
| Quality evaluation | EPA + DHA content (%) | 27.5 | 27.4 | 27.1 | 27.7 | 27.2 | 27.4 | 27.5 | 27.5 | 27.5 | 26.5 | 26.8 |
| | EPA + DHA residual ratio in neutralized oil (%) | 98.2 | 97.9 | 96.8 | 98.9 | 97.1 | 97.9 | 98.2 | 98.2 | 98.2 | 94.6 | 95.7 |
| | Oil odor immediately after preparation | 9 | 9 | 9 | 8 | 10 | 10 | 10 | 10 | 10 | 10 | 10 |
| | Fish odor immediately after preparation | 9 | 9 | 9 | 8 | 10 | 10 | 10 | 10 | 10 | 10 | 10 |
| | Rosemary odor immediately after preparation | 9 | 9 | 8 | 9 | 9 | 9 | 10 | 10 | 10 | 10 | 10 |
| | Degradation odor of oil after storage | 7 | 7 | 8 | 7 | 7 | 8 | 8 | 9 | 10 | 6 | 6 |
| | Fish odor after storage | 7 | 8 | 9 | 8 | 8 | 8 | 9 | 9 | 10 | 7 | 7 |
| | Reversion odor of rosemary after storage | 9 | 9 | 9 | 9 | 9 | 10 | 10 | 10 | 10 | 9 | 9 |
| | POV after storage (meq/kg) | 10.5 | 10.1 | 9.5 | 10.1 | 10.0 | 9.6 | 9.3 | 8.5 | 4.2 | 12.2 | 11.8 |

Examples 3 to 13 obtained by appropriately controlling the thermal history in the step of steam deodorization showed improved EPA+DHA residual ratio in bleached oil as 90% or more, and superior quality in both immediately after preparation and after storage than Examples 1 and 2.

In Examples 3 to 11, by adjusting 170° C. or more of temperature and 50 or less of thermal history in the step of steam deodorization, EPA+DHA residual ratio in neutralized oil was improved and more favorable values in the flavor evaluation and peroxide value, which is an index of oxidative stability of fat, after storage were obtained.

In Examples 7 to 11, by using activated carbon treated by chemical activation, especially activated carbon treated with phosphoric acid, further favorable values in the flavor evaluation and peroxide value, which is an index of oxidative stability of fat, after storage were obtained.

INDUSTRIAL APPLICABILITY

According to the present invention, a long-chain polyunsaturated fatty acid-containing fat having good flavor is obtained by a simple method, and a long-chain polyunsaturated fatty acid-containing fat wherein generation of reversion odor and unpleasant odor, and peroxide substance which adversely acts on health is suppressed for a long period of time, and having high health advantage is utilized for food, pharmaceutical composition, cosmetic, pet food, quasi drug and the like, by using the long-chain polyunsaturated fatty acid-containing fat of the present invention.

The invention claimed is:

1. A process for producing a long-chain polyunsaturated fatty acid- containing fat, comprising:
a step of contacting a fat with a rosemary,
a step of subjecting the fat and rosemary to an adsorption treatment with activated carbon,
then a step of removing the rosemary by a filtration, and
a step of steam deodorization of the fat after the filtration under reducing pressure,
wherein the fat comprises 3% by weight or less of water,
wherein the rosemary is a rosemary powder obtained by drying a leaf of Lamiaceae, genus *Rosmarinus* and pulverizing the dried leaf,
wherein the activated carbon is treated by chemical activation, and
wherein the steam deodorization temperature is 170° C. or more and the deodorization temperature meets the following formula:

(deodorization temperature−170° C.)×(deodorization temperature−170° C.)×deodorization time (minutes)/1000=50 or less.

2. The process for producing a long-chain polyunsaturated fatty acid-containing fat according to claim 1,
further comprising a step of bleaching before or at the same time as the step of contacting the fat with the rosemary, wherein the step of contacting is with stirring, and
wherein the step of filtration is after the step of bleaching, followed by the step of steam deodorization under reducing pressure.

3. The process for producing a long-chain polyunsaturated fatty acid-containing fat according to claim 1, wherein the water content in the fat is maintained at 3% by weight or less from the step of contacting the fat with the rosemary to the step of steam deodorization under reducing pressure.

4. The process for producing a long-chain polyunsaturated fatty acid-containing fat according to claim 2, wherein the step of bleaching is performed by adding 0.5% by weight or more of the rosemary and 1% by weight or more of activated earth.

5. The process for producing a long-chain polyunsaturated fatty acid-containing fat according to claim 1, wherein the fat comprises 20% by weight or more of long-chain polyunsaturated fatty acid having 5 or more double bonds in a constituent fatty acid composition.

6. The process for producing a long-chain polyunsaturated fatty acid-containing fat according to claim 1, wherein the chemical activation is phosphoric acid activation.

7. The process for producing a long-chain polyunsaturated fatty acid- containing fat according to claim 2, wherein peroxide value of the long-chain polyunsaturated fatty acid-containing fat after the step of steam deodorization is 14 meq/kg or less measured by the following storage test for a long-chain polyunsaturated fatty acid-containing fat:
(storage test for a long-chain polyunsaturated fatty acid-containing fat)
pouring 50 g of uniformly mixed fat into 100 ml glass container and then sealing the container,
storing the glass container at 40° C. for 14 days, and
measuring peroxide value of the fat after 14 days storage.

8. The process for producing a long-chain polyunsaturated fatty acid-containing fat according to claim 1, further comprising:
a step of bleaching before or at the same time as the step of contacting the fat with the rosemary, wherein the step of contacting is with stirring,
wherein the step of filtration is after the step of bleaching, followed by the step of steam deodorization under reducing pressure,
wherein the water content in the fat is maintained at 3% by weight or less from the step of contacting the fat with the rosemary to the step of steam deodorization,
wherein the step of bleaching is performed by adding 0.5% by weight or more and 10% by weight or less of rosemary, 1% by weight or more and 5% by weight or less of activated earth, and 1% by weight or more and 4% by weight or less of activated carbon,
wherein the fat comprises 20% by weight or more of long-chain polyunsaturated fatty acid having 5 or more double bonds in a constituent fatty acid composition.

9. The process for producing a long-chain polyunsaturated fatty acid-containing fat according to claim 8, wherein the chemical activation is phosphoric acid activation.

10. The process for producing a long-chain polyunsaturated fatty acid-containing fat according to claim 8,
wherein the water content in the fat is maintained at 1% by weight or less from the step of contacting the fat with the rosemary to the step of steam deodorization, and
wherein the step of bleaching is performed by adding 0.5% by weight or more and 5% by weight or less of rosemary, 1% by weight or more and 5% by weight or less of activated earth, and 1% by weight or more and 4% by weight or less of activated carbon.

11. The process for producing a long-chain polyunsaturated fatty acid-containing fat according to claim 6,
further comprising a step of bleaching before or at the same time of the step of contacting with the rosemary with stirring, and
wherein the step of filtration is after the step of bleaching, followed by the step of steam deodorization under reducing pressure.

12. The process for producing a long-chain polyunsaturated fatty acid- containing fat according to claim 8,
further comprising a step of adding a tea extract to the long-chain polyunsaturated fatty acid-containing fat,
wherein the chemical activation is phosphoric acid activation.

* * * * *